United States Patent [19]

Ogata et al.

[11] Patent Number: 4,607,038

[45] Date of Patent: Aug. 19, 1986

[54] OPHTHALMIC PRANOPROFEN COMPOSITIONS

[75] Inventors: Kazumi Ogata, Toyonaka; Yujiro Yamamoto, Suita; Yoshie Ozaki, Kobe, all of Japan

[73] Assignees: Yoshitomi Pharmaceutical Industries, Ltd.; Senju Pharmaceutical Co., Ltd., both of Osaka, Japan

[21] Appl. No.: 704,585

[22] Filed: Feb. 22, 1985

[30] Foreign Application Priority Data

Mar. 1, 1984 [JP] Japan .................................. 59-39763

[51] Int. Cl.$^4$ ...................... A61K 31/44; A61K 33/22
[52] U.S. Cl. .................................. 514/291; 424/148; 514/914; 514/922
[58] Field of Search ...................... 514/291, 914, 922; 424/148

[56] References Cited

FOREIGN PATENT DOCUMENTS 0082921  7/1983  European Pat. Off. .
2059768  4/1981  United Kingdom .

OTHER PUBLICATIONS

Chem. Abst. 100: 114735(g) (1984)—Takahashi et al.
Chem. Abst. 99: 169225(g) (1983)—Nao-i et al.
Chem. Abst. 97: 174680(q) (1982)—Ogawa et al.
Chem. Abst. 96: 129806(d) (1982)—Ringold et al.

Primary Examiner—Douglas W. Robinson
Attorney, Agent, or Firm—Berman, Aisenberg & Platt

[57] ABSTRACT

An ophthalmic solution having anti-inflammatory action without side effects and irritativeness which comprises pranoprofen and boric acid.

5 Claims, 1 Drawing Figure

●——● : Isotonic NaCl-dropping group
○——○ : Pranoprofen-dropping group
×——× : Dexamesazone-dropping group

4,607,038

OPHTHALMIC PRANOPROFEN COMPOSITIONS

FIELD OF THE INVENTION

This invention relates to an ophthalmic solution comprising pranoprofen and boric acid.

BACKGROUND OF THE INVENTION

In the ophthalmic field, at the present time, patients contracting inflammatory diseases account for more than half all the patients of eye diseases. As an ophthalmic solution administered to them, various kinds of medicaments, for example antibiotics, steroid compounds, non-steroid anti-inflammatory agents, FAD preparations, etc., are used. The antibiotics and FAD preparations are categorized under medicaments acting on the causes for inflammation of the eyes (namely, medicaments for causal treatment), whereas the steroid compounds and non-steroid anti-inflammatory agents are categorized under medicaments acting on the inflammation per se of the living body (namely, medicaments for symptomatic treatment).

The steroid compounds provide clinically superior effects on inflammatory eye diseases of the external and front ocular parts, and nowadays are clinically indispensable ophthalmic agents. In contradiction to these favorable effects, however, the compounds are known to have severe side effects, such as aggravation of steroid glaucoma, infectious eye diseases, particularly herpesvirus eye diseases, etc., so that, in the present situation, physicians clinically use them while having some apprehension of these side effects. The non-steroid anti-inflammatory agents are used clinically in conjunction with the steroid compounds or alone, but are unavoidably inferior to the steroid compounds with regard to efficacy. An attempt has been heretofore made to provide ophthalmic solutions containing non-steroid anti-inflammatory agents as a main ingredient, but most of them are so irritating to the eyes and so strongly painful to the eyes that they cannot be practically used as an ophthalmic solution.

Hence, ophthalmic agents for herpesvirus eye diseases have not yet been found.

A primary object of this invention is to provide an ophthalmic solution having potent anti-inflammatory action.

Another object of this invention is to provide an ophthalmic solution having no foregoing side effects and, accordingly, capable of being dropped in the eyes to treat herpesvirus ophthalmia.

A further object of this invention is to provide an ophthalmic solution having less irritative anti-inflammatory properties.

A still further object of this invention is to provide a method for treatment of herpesvirus ophthalmia.

SUMMARY OF THE INVENTION

With a view toward attaining the foregoing objects, namely: solving the prior art technical problems, the present inventors have investigated extensively and as a result, have accomplished this invention by finding out that combined use of pranoprofen selected from innumerable compounds having anti-inflammatory activity and boric acid selected from various kinds of isotonicity-imparting agents can solve completely all the foregoing problems.

According to this invention, there is provided an ophthalmic solution containing pranoprofen as an anti-inflammatory active ingredient and boric acid as an isotonicity-imparting agent.

According to another embodiment of this invention, there is provided an anti-inflammatory ophthalmic solution to herpesvirus ophthalmia containing pranoprofen as an active ingredient.

According to further embodiment of this invention, there is provided a method of treatment for herpesvirus ophthalmia comprising dropping an efficient amount of pranoprofen in the eyes.

DETAILED DESCRIPTION OF THE INVENTION

Figure 1:
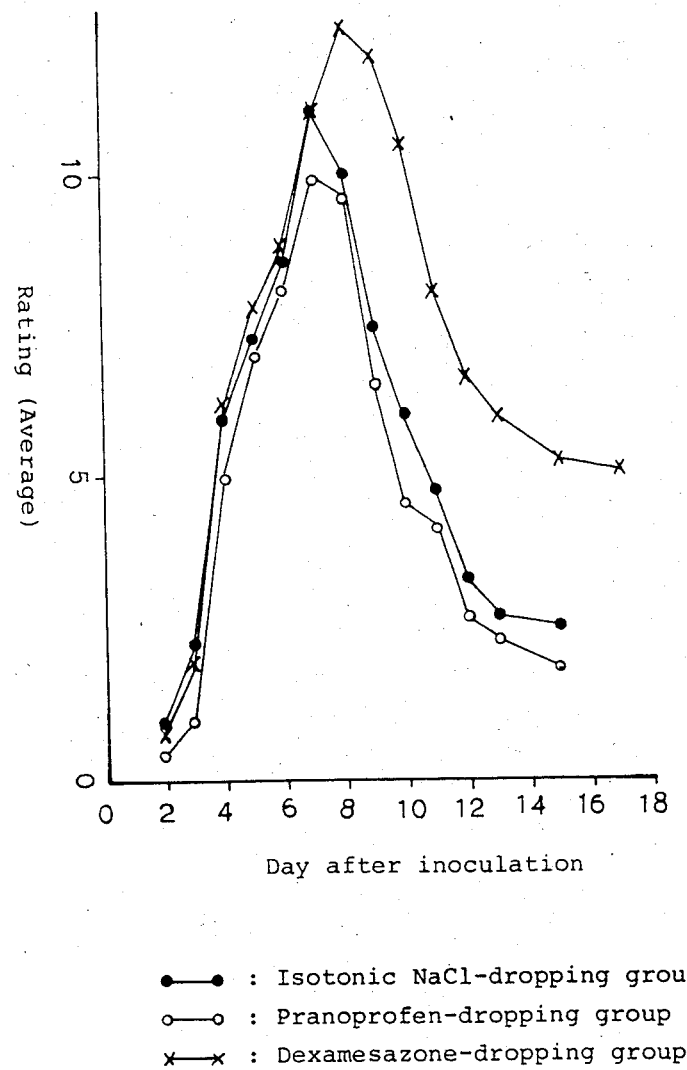

Pranoprofen whose chemical name is α-methyl-5H-[1]-benzopyrano[2,3-b]pyridine-7-acetic acid is a novel non-steroid anti-inflammatory agent synthesized and developed by Yoshitomi Pharmaceutical Industries, Ltd. (Japan). This was revealed to have, as a result of fundamental tests, remarkable anti-inflammatory, analgesic and anti-pyretic actions and a wide safety range. Furthermore, it was confirmed, as a result of clinical tests, to have superior effects on inflammatory diseases and pain reactions. Pranoprofen is now commercially available under the trade name of "Niflan" (registered trademark), and characteristics and method for preparation of it are disclosed in U.S. Pat. No. 3,931,205.

The present inventors, however, have found that pranoprofen itself has eye irritativeness as shown in subsequent Experimental Example 1 and the irritativeness can be solved by this invention.

The concentration of pranoprofen as an anti-inflammatory active ingredient is usually in the range of 0.01 to 0.5 (w/v)% and can be adjusted appropriately depending on the intended objects.

Boric acid is incorporated in such an amount that its osmotic pressure ratio is about 1, and in general, in an amount on the order of 0.5–2 (w/v)%.

An essential feature of this invention resides in the pranoprofen is selected as an active ingredient and boric acid is selected as an isotonicity-imparting agent, and accordingly, it will be readily understood that further ingredients known per se in the preparation of ophthalmic solutions are incorporated in a usual amount.

Specific examples of formulation ingredients other than those already referred to and preferred formulation amounts will be exemplified hereinbelow.

As a dissolution-assisting agent, there may be mentioned, for example, non-ionic surface active agents, such as polyoxyethylenesorbitan monooleate, polyoxyethyleneoxystearic acid triglyceride, polyethylene glycol, etc.

A thickening agent includes, for example, polyvinylpyrrolidone, methylcellulose, hydroxypropylmethylcellulose, hydroxyethylcellulose, hydroxypropylcellulose, etc.

As an ophthalmic antiseptic, those conventionally used may be mentioned, for example, benzalconium chloride, cetylpyridinium chloride, chlorobutanol, methylparaben, propylparaben, etc.

A chelating agent, such as sodium ethylenediaminetetraacetate (EDTA-Na), may be used.

The pH of the ophthalmic solution of this invention is preferred to be 6.5–8.5, particularly about 7.5.

The dosage of the anti-inflammatory active ingredient of this invention to be dropped in the eyes is an amount sufficient to render efficiently anti-inflammatory ophthalmia and may vary depending on the disease conditions, kind of inflammation, etc., but is generally 5-200 μg per dose. The administration frequency may be chosen appropriately in the range of 1 to 4 times a day. The foregoing amount and frequency to be dropped in the eyes are also true where pranoprofen is used for the treatment of ophthalmia ascribable to herpesvirus.

The effects and advantages of this invention will be hereinafter described.

EXPERIMENTAL EXAMPLE 1

In order to effect eye irritation test, its evaluation criterion was determined in the following manner. That is, Experimental Formula Examples 1, 2, 3 and 4 were dropped in the eyes of ten healthy men and compared with one another with respect to the degree of eye irritation.

Experimental Formula Example 1

An ophthalmic solution is prepared by dissolving 620 mg of sodium chloride into 100 ml of 0.04M phosphate buffer having a pH of 7.4 and filtering and pasteurizing the solution.

Experimental Formula Example 2

An ophthalmic solution is prepared by dissolving 660 mg of sodium chloride into 100 ml of 0.04M phosphate buffer having pH of 6.5 and filtering and pasteurizing the solution.

Experimental Formula Example 3

An ophthalmic solution is prepared by dissolving 680 mg of sodium chloride into 100 ml of 0.04M phosphate buffer having a pH of 5.5, and filtering and pasteurizing the solution.

Experimental Formula Example 4:

An ophthalmic solution is prepared by dissolving 680 mg of sodium chloride into 100 ml of 0.04M phosphate buffer having a pH of 4.5 and filtering and pasteurizing the solution.

TABLE 1

| Testing Person | Experimental Formula Ex. 1 | Experimental Formula Ex. 2 | Experimental Formula Ex. 3 | Experimental Formula Ex. 4 |
| --- | --- | --- | --- | --- |
| 1 | — | +1 | +2 | +4 |
| 2 | — | +1 | +3 | +4 |
| 3 | — | +1 | +2 | +3 |
| 4 | +1 | +2 | +3 | +4 |
| 5 | — | +1 | +2 | +2 |
| 6 | +1 | +2 | +3 | +4 |
| 7 | — | +1 | +3 | +3 |
| 8 | — | +1 | +2 | +4 |
| 9 | — | +1 | +2 | +4 |
| 10 | +1 | +1 | +3 | +4 |

From the test results of Table 1, the degree of irritation was evaluated according to the criterion:

|   |   | Rating |
| --- | --- | --- |
| — | No irritation, no unpleasant feeling (Experimental Formula Ex. 1 is dropped in the eyes.) | 0 |
| +1 | Slight irritation feeling (Experimental Formula Ex. 2 is dropped in the eyes.) | 1 |
| +2–+3 | Irritation feeling (Experimental Formula Ex. 3 is dropped in the eyes.) | 2-3 |
| +4 | Strong irritation feeling (Experimental Formula Ex. 4 is dropped in the eyes.) | 4 |

The following Experimental Formula Examples 5, 6, 7 and 8 were dropped in the eyes of ten healthy men and compared with one another in respect of eye irritation on the basis of this assessment criterion.

Experimental Formula Example 5

One hundred mg of pranoprofen and 850 mg of sodium chloride are dissolved in purified water, and sodium hydroxide is added to the solution and dissolved to adjust the pH to about 7.5. Thereafter, purified water is added to make the total amount of the solution 100 ml, and it is filtered and pasteurized to prepare an ophthalmic solution.

Experimental Formula Example 6

Pranoprofen, 100 mg, and 5000 mg of d-mannitol are incorporated in purified water, and sodium hydroxide is added and dissolved to adjust pH of the solution to about 7.5. Then purified water is added to make the total amount of the solution 100 ml, and it is filtered and pasteurized to prepare an ophthalmic solution.

Experimental Formula Example 7

Pranoprofen, 100 mg, and 2500 mg of conc. glycerine are incorporated in purified water, and to the solution is added and dissolved sodium hydroxide to adjust pH to about 7.5. Then purified water is added to make the total amount of the solution 100 ml, and the solution is filtered and pasteurized to prepare an ophthalmic solution.

Experimental Formula Example 8

Pranoprofen, 100 mg, and 1600 mg of boric acid are dissolved in purified water, and 800 mg of borax is added to adjust pH of the solution to about 7.5. Thereafter, purified water is added to make the total amount of the solution 100 ml, and it is filtered and pasteurized to prepare an ophthalmic solution.

TABLE 2

| Testing Person | Experimental Formula Ex. 5 | Experimental Formula Ex. 6 | Experimental Formula Ex. 7 | Experimental Formula Ex. 8 The Invention |
| --- | --- | --- | --- | --- |
| 1 | 3 | 2 | 2 | 0 |
| 2 | 2 | 2 | 2 | 0 |
| 3 | 3 | 3 | 3 | 2 |
| 4 | 3 | 1 | 2 | 1 |
| 5 | 4 | 3 | 3 | 1 |
| 6 | 3 | 3 | 3 | 2 |
| 7 | 2 | 2 | 2 | 0 |
| 8 | 4 | 4 | 4 | 2 |
| 9 | 3 | 3 | 3 | 0 |
| 10 | 2 | 2 | 3 | 0 |
| Total | 29 | 25 | 27 | 8 |
| Average | 2.9 | 2.5 | 2.7 | 0.8 |

From the results in Table 2, it will be apparent that irritativeness of the ophthalmic solution of this invention is statistically significant as compared with those of formulae each containing sodium chloride, d-mannitol and glycerine. Thus, the ophthalmic solution of this invention was corroborated to have low irritativeness.

EXPERIMENTAL EXAMPLE 2

What influences non-steroid pranoprofen and steroid dexamethasone have on cornea herpes inflammation of rabbits was examined.

Method:
Herpesvirus:
  50 μl of solution in which $6 \times 10^7$ PFU/ml is diluted to 10-fold is inoculated.
Group:
  Group to which 0.1% pranoprofen is dropped in the eyes (n=7)
  Group to which 0.05% dexamethasone is dropped in the eyes (n=7)
  Group to which isotonic sodium chloride solution is dropped in the eyes (n=6)
Dropping of ophthalmic solution in the eyes:
  One drop of ophthalmic solution is dropped in the eyes four times a day for five days before inoculation of virus.
Observation:
  Groups to which ophthalmic solution was dropped in the eyes are dyed with 1% Rose Bengal and rated according to the list of ratings of Kaufman et al [Archives of Ophthalmology, 69, 926 (1963)].
Results:

Results are illustrated in the accompanying FIG. 1 which is a graphical representation showing effects of ophthalmic solution according to this invention on herpesvirus inflammation.

As will be apparent from FIG. 1, the group to which pranoprofen was dropped in the eyes went through a curing process similar to that of the group to which isotonic sodium chloride solution was dropped in the eyes and did not effect on cornea herpes inflammation. On the other hand, the group to which dexamethasone was dropped in the eyes showed high peak ratings and a slow curing rate as compared with the group to which isotonic sodium chloride solution was dropped in the eyes.

From the results above, it is deemed that dexamethasone aggravates cornea herpes, but pranoprofen does not.

Example 1

One hundred mg of pranoprofen, 1600 mg of boric acid, 200 mg of polyoxyethylenesorbitan monooleate and 5 mg of benzalconium chloride are dissolved in purified water, and to the solution is added 800 mg of borax to adjust pH to about 7.5. Thereafter, purified water is added to make the total amount of the solution 100 ml, and it is filtered and pasteurized to prepare an ophthalmic solution.

Example 2

One hundred mg of pranoprofen, 1600 mg of boric acid, 26 mg of methyl paraoxybenzoate and 14 mg of propyl paraoxybenzoate are dissolved in purified water and 800 mg of borax is added thereto to adjust pH to about 7.5. Then, purified water is added to make the total amount of the solution 100 ml, and the solution is filtered and pasteurized to prepare an ophthalmic solution.

We claim:

1. An anti-inflammatory ophthalmic solution comprising (a) a therapeutically effective amount of pranoprofen and (b) an irritant-reducing amount of boric acid.

2. A process for preparing an ophthalmic solution which comprises dissolving a therapeutically effective amount of pranoprofen or an ophthalmologically-acceptable salt thereof and an irritant reducing amount of boric acid in an aqueous medium and adjusting the pH of the resulting solution to 6.5–8.5.

3. A process of reducing irritation of an eye to which a pranoprofen-containing anti-inflammatory aqueous ophthalmic solution is to be applied which comprises incorporating in the ophthalmic solution an amount of boric acid effective to reduce the irritating effect of the pranoprofen on the eye.

4. A process of treating herpesvirus ophthalmia which comprises dropping in an eye of a subject afflicted with herpesvirus ophthalmia an anti-inflammatory-effective amount of pranoprofen in an aqueous ophthalmic solution containing an amount of boric acid effective to reduce any irritating effect of pranoprofen on the eye.

5. A process according to claim 2 which further comprises pasteurizing the pH-adjusted aqueous medium.

* * * * *